United States Patent
Cabiri et al.

(10) Patent No.: US 10,071,198 B2
(45) Date of Patent: Sep. 11, 2018

(54) ADHESIVE STRUCTURE FOR MEDICAL DEVICE

(71) Applicant: MEDIMOP Medical Projects Ltd., Ra'anana (IL)

(72) Inventors: Oz Cabiri, Macabim-Reut (IL); Reuven Y. Filman, Netanya (IL); Boris Degtiar, Modiin (IL)

(73) Assignee: West Pharma. Servicees IL, Ltd., Ra'anana (IL)

( * ) Notice: Subject to any disclaimer, the term of this patent is extended or adjusted under 35 U.S.C. 154(b) by 311 days.

(21) Appl. No.: 13/667,739

(22) Filed: Nov. 2, 2012

(65) Prior Publication Data
US 2014/0128815 A1     May 8, 2014

(51) Int. Cl.
*A61M 5/158*     (2006.01)
*A61M 5/142*     (2006.01)

(52) U.S. Cl.
CPC ........ *A61M 5/158* (2013.01); *A61M 5/14248* (2013.01); *A61M 2005/14252* (2013.01); *A61M 2205/13* (2013.01)

(58) Field of Classification Search
CPC .... A61M 2005/14252; A61M 2205/13; A61M 5/14248; A61M 5/158
See application file for complete search history.

(56) References Cited

U.S. PATENT DOCUMENTS

| | | | |
|---|---|---|---|
| 1,795,630 A | 3/1931 | Wilson | |
| 2,860,635 A | 11/1958 | Wilburn | |
| 3,203,269 A | 8/1965 | Perrine | |
| 3,212,685 A | 10/1965 | Swan et al. | |
| 3,794,028 A | 2/1974 | Mueller et al. | |
| 3,994,295 A | 11/1976 | Wulff | |
| 4,195,636 A | 4/1980 | Behnke | |

(Continued)

FOREIGN PATENT DOCUMENTS

| | | |
|---|---|---|
| CN | 1224341 A | 7/1999 |
| CN | 1747683 A | 3/2006 |

(Continued)

OTHER PUBLICATIONS

Extended European Search Report dated Aug. 7, 2014 in EP Application No. 1417477.4.

(Continued)

*Primary Examiner* — Imani Hayman
(74) *Attorney, Agent, or Firm* — Panitch Schwarze Belisario & Nadel LLP

(57) ABSTRACT

A variable flexibility adhesive system may adhere a surface of a medical infusion device to the skin of a user. The system may be configured to hold a location on the surface stationary with respect to a site on the user's skin. The system may include an adhesive substrate for adhering to the user and an interface where the substrate is held to the surface of the device. The interface may totally and/or partially surround the stationary location. A skirt of the substrate may totally and/or partially surround the interface. Parts of the skirt may be stiffened. Optional features may include tabs for activation of the adhesive and/or a location for peeling the infuser away from the skin. Additionally or alternatively, the interface may have variable flexibility. Additionally or alternatively, the stiffener may include a plastic layer.

24 Claims, 10 Drawing Sheets

(56) References Cited

U.S. PATENT DOCUMENTS

| | | |
|---|---|---|
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,149,614 A * | 11/2000 | Dunshee ............... A61F 13/023 206/440 |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |

(56) References Cited

U.S. PATENT DOCUMENTS

| | | |
|---|---|---|
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1* | 10/2002 | Ramey ............. A61M 5/158 604/164.07 |
| 2002/0169215 A1 | 11/2002 | Meng |

(56) References Cited

U.S. PATENT DOCUMENTS

| | | |
|---|---|---|
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0123819 A1 | 5/2007 | Mernoe et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234805 A1 | 9/2010 | Kaufmann et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |

(56) References Cited

U.S. PATENT DOCUMENTS

| | | |
|---|---|---|
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 1863566 A | 11/2006 |
| CN | 1929884 A | 3/2007 |
| CN | 101090749 A | 12/2007 |
| CN | 101460207 A | 6/2009 |
| CN | 101970033 A | 2/2011 |
| CN | 201941304 U | 8/2011 |
| CN | 102186733 A | 9/2011 |
| CN | 102256657 A | 11/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 06069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2013/173092 A1 | 11/2013 |
| WO | 2014/070453 A1 | 5/2014 |
| WO | 2014179774 A1 | 11/2014 |

OTHER PUBLICATIONS

Office Action dated Aug. 6, 2014 in EP Application No. 11 707 942.6.

Office Action dated Sep. 2, 2014 in JP Application No. 2012-550069.

(56) References Cited

OTHER PUBLICATIONS

Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312; Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
International Preliminary Report on Patentability dated Jul. 5, 2011 in International Application No. PCT/US2009/069552; Written Opinion.
Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.
Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability dated Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
U.S. Appl. No. 14/593,051 by Gross, filed Jan. 9, 2015.
Office Action dated Jan. 8, 2013 in JP Application No. 2010-527595.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
English translation of an Office Action dated Jan. 30, 2013 in CN Application No. 200880117084.X.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
U.S. Appl. No. 14/683,193 by Cabiri, filed Apr. 10, 2015.
Office Action dated Feb. 20, 2015 in U.S. Appl. No. 13/521,181 by Cabiri.
Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 23, 2014 in U.S. Appl. No. 13/472,112 by Cabiri.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/472,112 by Cabiri.
Office Action dated Nov. 21, 2014 in U.S. Appl. No. 13/429,840 by Cabiri.
Int'l Preliminary Report on Patentability dated Nov. 27, 2014 in Int'l Application No. PCT/US2013/039465.
Office Action dated Oct. 9, 2013 in IL Application No. 208634.
Office Action dated Nov. 5, 2013 in JP Application No. 2010-527595.
Office Action dated Sep. 29, 2013 in CN Application No. 201080040968.7.
Office Action dated Nov. 4, 2013 in EP Application No. 11 709 234.6.
Office Action dated Dec. 17, 2013 in JP Application No. 2012-529808.
Office Action dated Dec. 10, 2013 in CN Application No. 201180006567.4.
Office Action dated Jan. 8, 2014 in U.S. Appl. No. 13/521,167 by Cabiri.
U.S. Appl. No. 29/479,307 by Norton, filed Jan. 14, 2014.
Office Action dated Jul. 31, 2015 in U.S. Appl. No. 13/521,181 by Cabiri.
Office Action dated Aug. 13, 2015 in U.S. Appl. No. 14/553,399 by Cabiri.
Notice of Allowance dated Aug. 24, 2015 in U.S. Appl. No. 29/479,307 by Norton.
Daikyo Crystal Zenith® polymer, Manufactured by Daikyo Seiko, Ltd. (Jun. 25, 2008).
Copaxone®, Manufactured by Teva Pharmaceutical Industries Ltd. (2009).

(56) References Cited

OTHER PUBLICATIONS

Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action dated May 1, 2015 in U.S. Appl. No. 14/638,525 by Filman.
Office Action dated Jan. 15, 2016 in U.S. Appl. No. 13/472,112 by Cabiri.
Office Action dated Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action dated Sep. 18, 2015 in U.S. Appl. No. 13/874,085 by Cabiri.
Office Action dated May 24, 2017 in CN Application No. 2013800571961.
Office Action dated Nov. 2, 2016 in CN Application No. 2013800571961.
Search Report dated Nov. 2, 2016 in CN Application No. 2013800571961.
Office Action dated Sep. 13, 2017 in EP Application No. 13783458.6.

* cited by examiner

ADHESIVE STRUCTURE FOR MEDICAL DEVICE

BACKGROUND OF THE INVENTION

The present invention, in some embodiments thereof, relates to a method and system for attaching a device to a pliable surface and, more particularly, but not exclusively, to a method and system to attach a medical device to skin using a partially attached, variable stiffness adhesive system.

U.S. Pat. No. 6,585,707 to Cabiri discloses a system adapted to be disposed between a rigid or semi-rigid device and human skin for reliably attaching the device to the skin for an extended period of time. The system of Cabiri '707 includes a skin-contacting surface for adhering to human skin, and an opposed surface for attachment to a rigid or semi-rigid device. The system is attached along its opposed surface to a portion of the total area of the adjacent surface of the device. When the device is subjected to external stress, the stress is transmitted through the area of attachment and distributed to the unattached area. This minimizes stress on the skin and reduces the chance of detachment from the skin.

United States Patent Application No. 2007/0219597 discloses an adhesive patch system that may be used for affixing a pump or other object to a human body. Such an adhesive patch system may include two sets of adhesive members, each member including an adhesive material on at least one side so as to attach to the body. The members of the first set are spaced to allow the members of the second set to attach to the body in spaces provided between the members of the first set, and the members of the second set are spaced to allow members of the first set to detach from the body without detaching the members of the second set.

U.S. Pat. No. 8,025,658 discloses an adhesive patch of a medical device that may have selective areas with adhesive material of varying adhesion strengths. In other embodiments, an adhesive patch of a medical device may include adhesive material that may be activated by a catalyst to increase or decrease the adhesion strength of the adhesive material. In further embodiments, a medical device may include a pierceable membrane containing an agent, the pierceable membrane positioned to be pierced by a needle and to cause some of the agent to be carried to the user-patient.

U.S. Pat. No. 7,837,651 discloses a drug delivery infusion pump assembly which may include a cannula assembly comprising a cannula, which is disposable on the face of a patient, and which includes left and right cannula support wings each having a wing tip portion with an adhesive pad removably adhesively attachable to a side of the face of the patient. The adhesive pad may provide a more convenient cannula attachment for the patient than a conventional headband.

Additional background art includes adhesives for EKG electrodes and other electronic sensors having rigid and semi rigid bodies with sensing areas and or operational areas that touch or are inserted into the skin

SUMMARY OF THE INVENTION

According to an aspect of some embodiments of the present invention there is provided a system for anchoring a location on a surface of a medical infusion device to the skin of a user. The system may include an adhesive substrate for adhering to the skin of the user and an interface attaching the substrate to the surface of the device. The substrate may include a skirt extending beyond the interface. The skirt may be flexibly attached to the interface. The system may further include a stiffener stiffening a portion of the skirt. The stiffener may be less flexible than the substrate.

According to some embodiments of the invention, the stiffener may inhibit folding of the skirt under an out of plane bending force.

According to some embodiments of the invention, the out of plane bending force may include gravity.

According to some embodiments of the invention, the stiffener may be stiff enough to suspend the skirt against a gravity force.

According to some embodiments of the invention, the stiffener may be biased away from a skin attaching surface of the substrate.

According to some embodiments of the invention, the stiffener may extend the skirt away from the infusion device.

According to some embodiments of the invention, the stiffener may hold the substrate taut.

According to some embodiments of the invention, the system may further include an adhesive cover, and a tab for peeling the adhesive cover from the substrate. The stiffener may support the substrate adjacent to the tab, supplying an opposing force when peeling the cover away from the substrate.

According to some embodiments of the invention, the tab may be located on the skirt.

According to some embodiments of the invention, the stiffener may be stiff enough to resist a force on the substrate caused by peeling of the cover.

According to some embodiments of the invention, the system may further include a start location for removal of the adhesive system from the user. The stiffener may extend along a peeling line to the start location, facilitating removing of the adhesive from the user's skin.

According to some embodiments of the invention, the start location may be on the skirt.

According to some embodiments of the invention, the stiffener includes a sharp turn between the peeling line and the interface.

According to an aspect of some embodiments of the present invention there is provided a system for anchoring a medical infusion device to a skin of a recipient. The system may include an adhesive substrate configured for adhering to the skin of the user. The system may further include a location on a surface of the device to be held firmly to the skin of the user, and a multi-part adhesive cover. The system may further include a first tab for peeling a first part of the cover and a second tab for peeling a second part of the cover. The first tab may be located beside the second tab and the first tab may be separated from the second tab by a notch.

According to some embodiments of the invention, the notch may be wedge shaped.

According to some embodiments of the invention, the notch may be triangular.

According to some embodiments of the invention, the stiffener may interpose between at least a part of the surface and a remaining portion of the substrate.

According to some embodiments of the invention, the stiffener may extend beyond a boundary of the surface.

According to some embodiments of the invention, the substrate may extend beyond a boundary of the stiffener.

According to some embodiments of the invention, the substrate may be divided into a plurality of discrete portions. Each of the portions may be joined to a separate respective subsurface of the surface.

According to some embodiments of the invention, a portion of the stiffener may interpose between the interface and the substrate.

According to some embodiments of the invention, the location to be held stationary may include a needle insertion point and/or a sensor.

According to some embodiments of the invention, the interface may surround the stationary location on at least two sides.

According to some embodiments of the invention, the interface may surround the stationary location on at least three sides.

According to some embodiments of the invention, the interface may surround the stationary location completely.

According to some embodiments of the invention, the substrate may interpose between the stiffener and the interface.

According to some embodiments of the invention, the stiffener may include one or more ribs extending from the interface toward an edge of the substrate.

According to some embodiments of the invention, an unbacked section of the substrate may be surrounded on at least two sides by the stiffener.

According to some embodiments of the invention, the stiffener may be attached to the surface of the device and the substrate may be affixed to the stiffener.

According to some embodiments of the invention, an unbacked skirt of the substrate may surround the surface on at least two sides.

According to some embodiments of the invention, an unbacked skirt of the substrate may surround the surface on at least three sides.

According to some embodiments of the invention, an unbacked skirt of the substrate may surround the surface on all sides.

According to some embodiments of the invention, wherein the substrate is may not be directly attached to the surface.

According to some embodiments of the invention, the surface may be protected from inadvertent adhesion to the substrate.

According to an aspect of some embodiments of the present invention there is provided a system to remove a plurality of adhesive covers from an infusion device. The system may include a plurality of pull tabs, and at least one notch separating between two of the plurality of tabs.

According to an aspect of some embodiments of the present invention there is provided a method of installing an adhesive to a medical infusion device. The method may include attaching part of a stiffener layer to a surface of the device and affixing an adhesive substrate to the layer.

According to some embodiments of the invention, the method may further include leaving another portion of the substrate unbacked by the stiffener.

According to some embodiments of the invention, the attaching may be on at least three sides of a location to be held firmly with respect to a site on the skin of the user.

According to some embodiments of the invention, the interface may include at least one relatively flexible region at least one less flexible region.

According to an aspect of some embodiments of the present invention there is provided a system for anchoring a location on a surface of a medical infusion device to the skin of a user. The system may include a flexible adhesive substrate for adhering to the skin of the user and an interface attaching the substrate to the surface of the device. The interface may include at least one relatively flexible region and at least one less flexible region.

According to some embodiments of the invention, interface may be attached to a portion of the substrate.

According to some embodiments of the invention, the system may further include a stiffener affixed to an unattached portion of said substrate.

According to some embodiments of the invention, the system may further include an adhesive cover, and a tab for peeling the adhesive cover from the substrate. The stiffener may support the substrate adjacent to the tab, supplying an opposing force when peeling the cover away from the substrate.

According to some embodiments of the invention, the system may further include a start location for removal of the adhesive system from the user. The stiffener may extend along a peeling line to the start location, facilitating removing of the adhesive from the user's skin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

Overview

Figure 1:
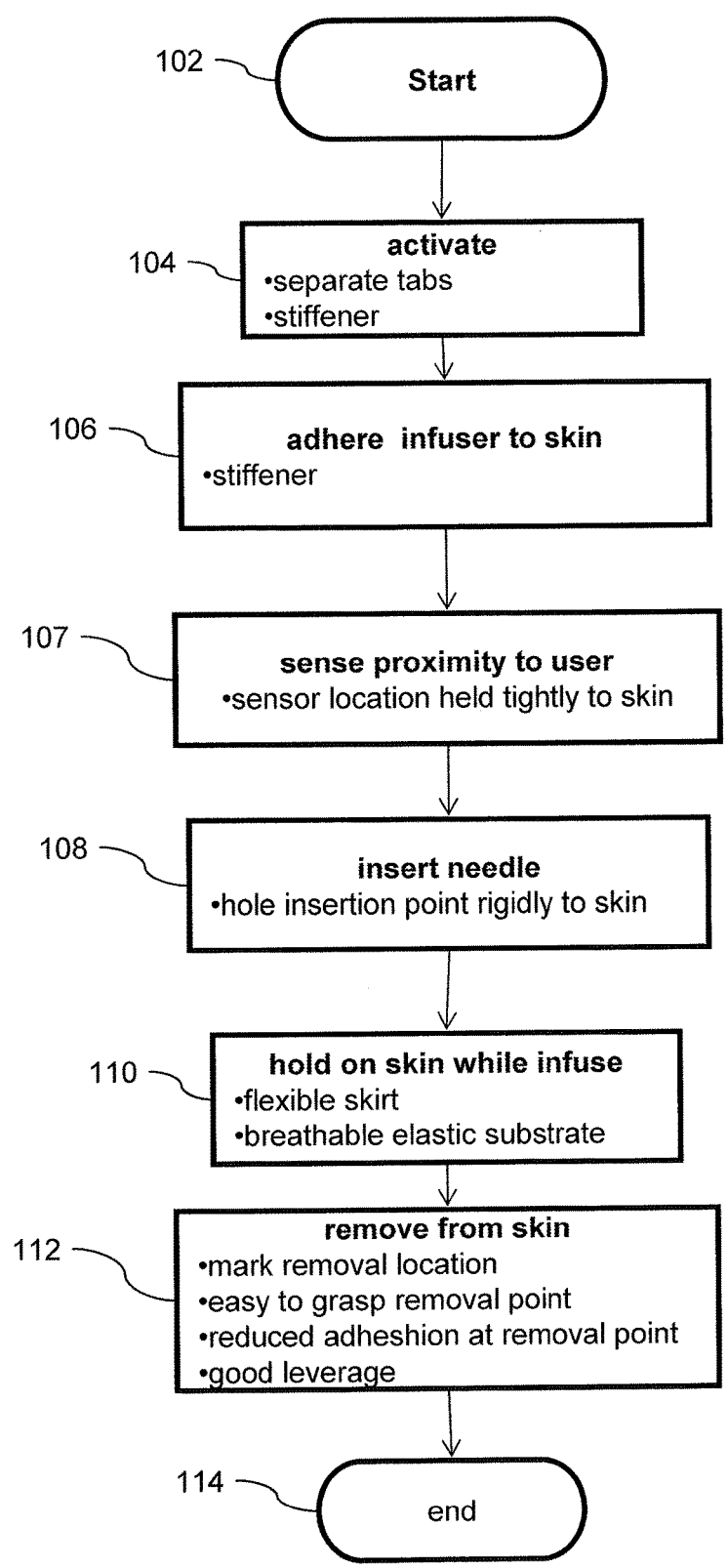
FIG. 1 is a flow chart illustration of an exemplary embodiment of a method of adhering a medical device to a user's skin.

The present invention, in some embodiments thereof, relates to a method and system for adhering a device to a pliable surface and, more particularly, but not exclusively, to a method and system to adhere a medical device to skin using a variable stiffness adhesive system.

An aspect of some embodiments is that the adhesive system may optionally be configured to anchor a part of the device to a fixed site on the user's skin. In some embodiments, a location on the device surface that is intended to be anchored to the user's skin may be totally surrounded and/or surrounded on at least two and/or three side by an interface attaching the surface to the adhesive system.

An aspect of some embodiments is that the adhesive system may optionally include a skirt region extending beyond the attaching interface. Optionally, the skirt region may be configured to have variable flexibility and/or elasticity and/or absorbency and/or breathability and/or adhesion.

Some surfaces adhered rigidly against a human skin may tend to detach for a few reasons including. For example, the weight of the device applied at a center of gravity at some distance from the skin surface may tend to peel the top edge of the device away from the skin. For example, the adhesive and/or the substrate may irritate the skin by retaining moisture and/or by applying stress forces and/or by preventing access to air. Irritation may cause the skin to slough off surface cells and the adhesive adhered to them. For example, as the skin stretches and/or flexes one part of the adhesive may be leveraged against another part, tearing the device away the adhered skin. Optionally, the flexible skirt region may reduce detachment associated with rigid and/or sealed surfaces, for example for one or more of reasons numerated above.

An aspect of some embodiments is that in the skirt region, the adhesive may optionally be applied to a substrate. Optionally the substrate may be breathable and/or absorbent and/or flexible and/or elastic. Alternatively or additionally the substrate may include a foam, for example flexible foams manufactured by Kendall Polychem or and Avery Dennison. Some examples of foams include Actiflex (made by Kendall Polychem and PVC1, a PVC closed cell foam made by Avery Dennison under the model number Q527297, or be made of woven and non-woven fabrics for example 3M#1776 0.3 mm White Spunlace Polyester Nonwoven with layer Acrylate and/or, Sontara marketed by Du Pont.

An aspect of some embodiments is that some locations the skirt may optionally include a stiffener. The stiffener may include, for example, a flexible plastic layer lending support to the substrate. Optionally the stiffener may be stiffer than the adhesive substrate but flexible enough to conform to the skin of the user. Alternatively or additionally, the stiffener may include a resin applied to stiffen certain parts of the adhesive substrate. In some embodiments, the stiffener may include a rib and/or a bend.

An aspect of some embodiments is that the stiffener may optionally be made of plastic, for example Polyethylene terephthalate (PET) having a thickness that may range for example between 0.1 and 0.8 mm. Other materials may also be used include for example Polycarbonate and/or ABS.

An aspect of some embodiments is that a skirt may optionally project beyond the edge of the device. For example the skirt may project for a minimum distance ranging between 2 to 30 mm. The maximum length of the skirt beyond the edge of the device may range for example between 15 and 30 mm. Optionally, the skirt may have a maximum length at the removal point from which the adhesive is configured to be peeled from the user's skin.

Optionally, the stiffener may support the substrate from out of plane bending forces and/or extend the substrate outward. Optionally, the stiffener may be designed to prevent the adhesive substrate from folding up or sticking to itself before adhesion to the user. Alternatively or additionally, the stiffener may help stabilize the device on the user's skin.

An aspect of some embodiments is that the device may be for example an infuser. Optionally, a part of the infuser held substantially stationary with respect to a fixed point on the user's skin may include, for example a needle insertion point. Optionally, the location may be held substantially stationary in the direction perpendicular to the skin surface (the needle may remain inserted at a substantially fixed depth that may range for example between 0.3 and 7.5 mm). Alternatively and/or additionally a device may be anchored to hold a needle substantially stationary in a lateral plane. In some embodiments, the needle may be held at an insertion angle that ranges for example between 20 and 90 from plane of the skin surface. Permissible fluctuations of the insertion angle may range between ±7 degrees. In some embodiments, fluctuations in the insertion depth (along the axis of the needle) during infusion may range, for example, between 0.1 and 0.5 mm.

An aspect of some embodiments is that an adhesive system may optionally be configured to anchor a sensor to a testing site on the user's skin. For example, the device may include a skin proximity sensor. Optionally, the adhesive may anchor the device holding the proximity sensor in constant contact with the user's skin. Additionally or alternatively, the adhesive may anchor the device holding a sensor stationary with respect the user's skin (for example the sensor may be held in the range of 0-25 degrees from the plane parallel to the surface of the skin and/or the sensor may be held at a fixed distance and/or depth±1.5 mm from the surface of the user's skin).

An aspect of some embodiments is that they may optionally include a preferred removal point. Optionally, at the removal point, the adhesive system may be configured to make it easy to grasp the adhesive and peel off the user's skin. For example, the stiffener may broaden near the removal point. Optionally, the stiffener may be shaped to lead outward from the interface and then turn sharply toward the removal point. Alternatively and or additional the adhesive may be lacking and/or reduced at the removable point. Optionally, the removal point may be marked for easy recognition.

An aspect of some embodiments is that a portion of the adhesive may optionally be protected from sticking to the adjacent surface of the device. Optionally the edge of the adhesive may be protected from sticking to adjacent surface, for example, by extending the edge of the adhesive beyond the adjacent surface of the device and/or by the stiffener intervening between the edge of the adhesive and the adjacent surface of the device.

An aspect of some embodiments is that a multipart protective cover may optionally be supplied for the adhesive surface. The protective cover may include one or more tabs for peeling off respective discrete parts of the cover. Optionally the tabs may be separated by one or more notches. In some embodiments, the width of the notch may range for example between 0.1 and 1 mm. In some embodiments, the length of the notch may range for example between 15-30 mm. Optionally, the shape of the notch may depend upon the form of the tabs. For example the notch may have a wedge and/or a triangular shape. In some embodiments, the stiffener may be configured to facilitate peeling of the cover from the adhesive. For example, the stiffener may supply extra support to the substrate at the tab location. For example the stiffener may prevent the substrate from bending more than 5 degrees when the cover is peeled from the substrate.

An aspect of some embodiments is that the interface connecting the adhesive substrate to the infuser may have a variable stiffness.

Exemplary embodiments of the invention are described in terms of an infusion device. It is understood that various other devices may also use an adhesion system as described herein. Unless stated otherwise, embodiments of the current invention should include various infusion devices, and/or other devices, for example iontophoretic drug delivery systems; minimally invasive sensors, including glucose sensors; diagnostic devices such as devices used in heart rate, pulse and ECG monitoring; ostomy products; nerve stimulators; external programming, data collection and monitoring devices for pace makers and defibrillators; implantable hearing aids and the like.

In some embodiments the adhesive system may be detachable from the infusion device. In some embodiments, a needle assembly may be attached to the injector via a flexible tube. Optionally, the needle assembly may be adhered independently of the body of the user.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Adhering a Device to Skin

FIG. 1 is a flow chart showing steps in adhering an infusion device to the skin of a user. Some advantageous aspects of the adhesion system of the current invention will be enumerated as they relate to each act of adhering the device.

Adhering a device may start 102, for example by activating 104 the adhesive. Activating 104 the adhesive may include for example, removing a protective cover from an adhesive. Alternatively or additionally, activation 104 may include attaching an adhesive system to the infuser and/or putting a catalyst on an adhesive substrate.

In some embodiments of the present invention, the protective cover may be made of multiple sheets each sheet covering part of the adhesive. Optionally each sheet may have a separate pull tab. The tabs of the sheets may be located one next to the other with a notch separating between tabs of different sheets. In some embodiments, the notch may make their removal of the sheets more intuitive.

In some embodiments a stiffener may help prevent the adhesive substrate from folding up. Optionally, a portion of the stiffener may be located near the location from which the protective layer is to be peeled. Optionally, the stiffener may be thicker or wider at the location from which the adhesive cover is to be peeled. For example, the stiffener may include a rib which extends to the location of a pull tab from which the protective cover is to be peeled. In some embodiments, the form of the stiffener may make it easier to peel off the protective cover. For example, the stiffener may steady the adhesive as the user pulls away the cover. Alternatively or additionally, the adhesive and the stiffener may be configured to avert the adhesive contacting and/or sticking to the surface of the infuser.

The shape of the cover may be configured such that the pull tab provides good leverage for pulling off the whole cover. Optionally, the pull tab may be located close areas of exceptionally peeling difficulty. Optionally, there may be multiple tabs to provide improved leverage to multiple areas of the cover.

In some embodiments, after removing the protective cover, the device may be adhered 106 to the skin of the user.

In some embodiments, once the infuser is adhered 106 to the user, the infuser will sense its proximity 107 to the user. For example, the infuser may include an optional proximity sensor. The proximity sensor may include, for example, a mechanical switch, an optical sensor, a heat sensor, and/or an electrical resistance sensor. Optionally, the adhesive may be configured to hold tightly to the skin of the user at the location of the proximity sensor. Optionally, the infuser and/or the adhesive may be configured to avoid the user's skin folding at the location of the proximity sensor and/or the needle insertion point.

In some embodiments, a needle may be inserted 108 into the user. Alternatively or additionally there may be a catheter and/or a needless delivery system. Optionally, at the insertion point, the infuser may be held stationary with respect to the user's skin by the adhesive. Holding the insertion point stationary may, for example, avoid the needle moving in the skin, being removed, or causing unnecessary pain.

In some embodiments, once infusion has begun, the adhesive may hold 110 the infuser stably to the user until infusion finishes. The adhesive may have optional properties that increase the stability of the adhesion. For example, the adhesive substrate may be flexible and/or stretchable, for example to reduce strain on the adhesive when the user moves. For example, the adhesive substrate may be breathable and/or absorbent, for example to reduce skin irritation and resultant sloughing. In some embodiments, the stiffener may enhance the mechanical connection between some locations on the adhesive and the infuser.

Optionally, adherence to the skin may be enhanced by the presence of a flexible adhesive skirt around the area where the adhesive is rigidly and/or semi-rigidly attached to the infuser. The weight of the infuser may be applied to the skirt region as a sheering stress rather than a peeling stress. The skirt may optionally reduce the probability that the infuser will spontaneously peel off the user.

In some embodiments, the adhesive may be supported by a flexible substrate. Optionally the substrate may have properties that improve adherence to the skin and/or reduce skin irritation. Optionally, the substrate may comply with the skin. For example the substrate may be flexible and/or elastic and/or breathable and/or absorbent. Optionally, in some locations, the substrate will be free to stretch or flex. Optionally, at some locations, the substrate will be supported by a stiffener. The stiffener may, for example make it easier to apply the adhesive to the skin and/or the stiffener may enhance the mechanical connection between the infuser and a peripheral area of the adhesive.

In some embodiments, after infusion has finished, the infuser may be removed 112 from the user. Optionally, the adhesive system may be designed to facilitate removal 112.

For example, there may be an intuitive mark of a preferred removal point. For example, there may be enhancements to make it the removal location easier to grasp and/or reduce the adhesion at removal location. The geometry of the adhesive may be configured so that the removal location has good leverage for removal of a large portion of the adhered surface.

After removal 112, infusions may optionally end 114 and the infuser may optionally be disposed of, for example by throwing it into the municipal garbage and/or into medical and/or hazardous waste.

Exemplary Infuser Having a Skin Sensor Near Edge

FIGS. 2A-4C illustrate an exemplary embodiment of an infuser having a proximity sensor near the edge of the infuser. The exemplary embodiment illustrates various geometric features of the adhesive system that lend extra support to particular areas. For example, an adhesive skirt may be provided. Optionally near the sensor, the skirt may be stiffened and/or widened, for example to help hold the sensor firmly against the skin of the user. Optionally, ribs of stiffener may prevent the adhesive from folding over and sticking onto itself. Alternatively or additionally, the adhesive and/or the stiffener may be configured to make it easier to peel a cover off of the adhesive and/or to make it easier to remove the device from the user, for example, after use.

Figure 2A:
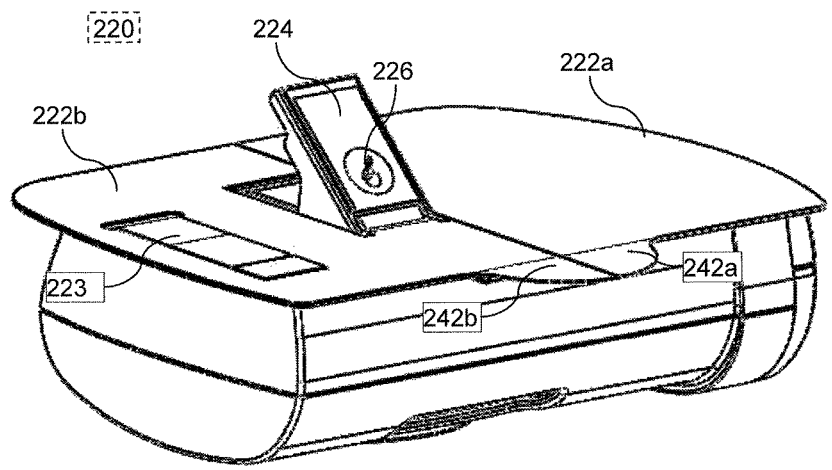
FIG. 2A is a view of an infuser from a first perspective showing an adhesive cover on a surface configured for attaching adjacent to a user's skin.
Figure 2B:
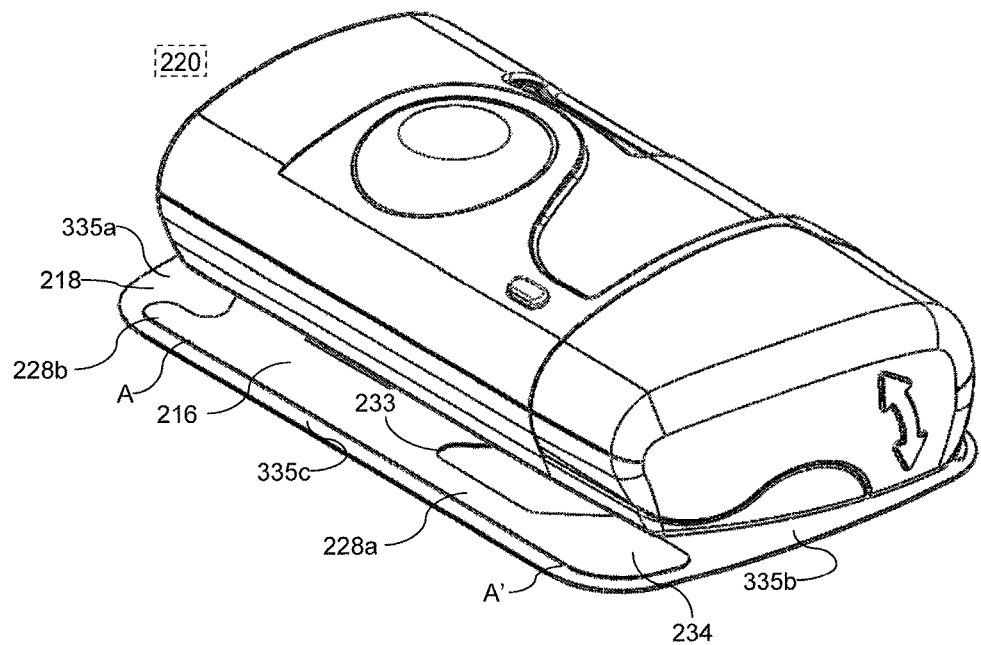
FIG. 2B is a is a perspective view of a infuser from a second perspective.

FIGS. 2A and 2B are perspective illustrations of an exemplary embodiment 220 of an infuser. The view of FIG. 2A shows the adjacent surface intended for adhesion to the user facing up, towards the viewer. In the view of FIG. 2B the adjacent surface intended for adhesion to the user faces downward, away from the viewer. FIGS. 2A and 2B illustrate exemplary external geometry of a device and the relationship between the parts.

Some embodiments may include an optional sensor, for example a mechanical skin proximity sensor 224. Optionally, sensor 224 may include a needle insertion point 226. In exemplary embodiment 220, proximity sensor 224 is located near the edge of the injector.

Optionally, for example as illustrated in FIG. 2B, a skirt of adhesive substrate 218 may extend beyond the adjacent surface. In some embodiments, a stiffener 216 may support the skirt. For example, in FIG. 2B a rib 228a supports an area 335b,c of the skirt from folding downward due to an out of plane bending force, for example gravity. For example, when the infuser is held adhesive side down, stiffener 216 may suspend the skirt. For example the skirt may bend downward to an angle of for example less than 10 degrees. Alternatively or additionally, parts of the stiffener may optionally be biased towards and/or away from the skin contact side of the adhesive. For example in FIG. 2B stiffener 216 may, for example, parts of the stiffener may be biased downward and/or upward.

Optionally, near proximity sensor 224 the skirt may be wider and/or include extra stiffener 216. In some embodiments, stiffener 216 may help hold proximity sensor 224 tightly against the skin of the user. In some embodiments, the stiffened skirt may help to avoid sensor 224 falsely registering removal of the device from the skin, for example when the user twists or moves.

In some embodiments, stiffener 216 may extend a skirt of substrate 218 away from the infuser. For example, stiffener 216 includes ribs 228a,b. Optionally, ribs 228a,b may serve for example to extend substrate 218 away from the infuser. Extending the skirt may, optionally, prevent substrate 218 from folding over onto itself, for example, before being attached to a user.

In some embodiments, sections of adhesive substrate 218 may not be backed by stiffener 216 and/or may not be attached to the surface of the injector. In some embodiments, the unbacked adhesive substrate 218 may be more flexible and/or elastic and/or breathable than the areas with backing. In the exemplary embodiment 220, for example, the edges of the skirt and some internal regions of the adhesive substrate are unbacked.

Optionally, rib 228a may widen near an edge which is to be used as a start location 234 for removal of the infuser from the user. For example, after infusion has finished a user may grasp location 234 and peel the infuser off his skin. The widening of rib 228a may, in some embodiments, may it easier to grasp the adhesive substrate to peel it off of the skin of the user. Alternatively or additionally stiffener 216 may extend beyond adhesive substrate 218 at removal location 234. Alternatively or additionally, the adhesive may be reduced, removed, and/or covered near removal location 234. In the exemplary embodiment of FIG. 2B, rib 228a runs along an edge of the skirt of substrate 218. Optionally, rib 228a is configured so that when location 234 is peeled away from the user's skin, the peeling force is distributed along a peeling line A-A' (for example the outer edge of the rib 228a), facilitating removal of the entire adhesive system from the user's skin. Alternatively or additionally, the peeling line may be straight line and/or a curved. In some embodiments, stiffener 216 may be connected to the infuser at an interface. The path along the stiffener from the interface to the removal start location 234 may include a sharp turn 233. For example, in the exemplary embodiment of FIG. 2B, turn 233 is approximately 100 degrees. Optionally, a turn between an interface connecting the stiffener to the infuser and the removal point may range, for example, between 45 and 135 degrees.

In FIG. 2A an exemplary two part adhesive cover 222a,b is shown having two peeling tabs 242a,b. Optionally, each peeling tab 242a,b may give improved leverage to peel a corresponding part of adhesive cover 222a,b as compared to a single peeling tab. For example, tab 242b may give good leverage to remove a battery insulator 223. Peeling tabs 242a,b may, optionally, extend out from the edge of the injector to make it easier for a user to locate the peeling location. Optionally, peeling tabs 242a,b may be located one next to the other to make it easier for the user to recognize them. In some embodiments, the tabs may extend away from the edge of the infuser ranging for example between 15 mm and 30 mm.

Figure 3:
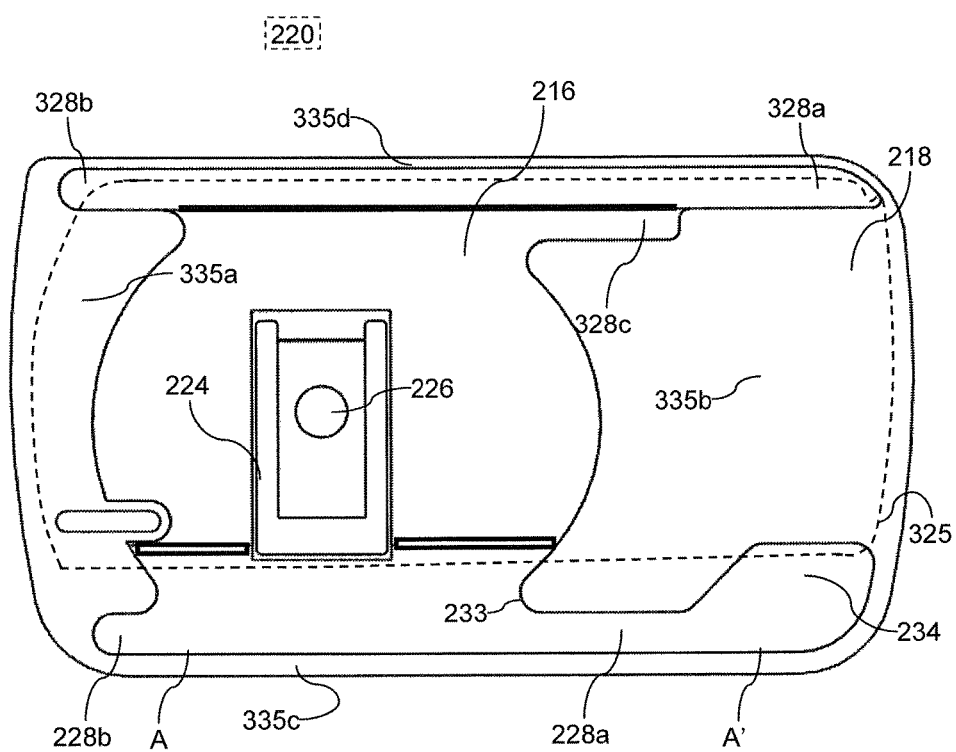
FIG. 3 is a cutaway projection of a stiffener layer of an adhesive system attached to an infuser.

Optionally, the geometry of the adhesive system may be configured to make peeling off the adhesive cover easier and/or more intuitive. For example, near the peeling location, the adhesive matrix may be stiffened by the stiffener and/or by an interface to the infuser FIG. 3 illustrates a cutaway view of stiffener 216 of embodiment 220. The edge 325 of the adjacent surface of the injector is illustrated by a dashed line. In exemplary embodiment 220 stiffener 216 is attached to the adjacent surface of the infuser near proximity sensor 224 and needle insertion point 226.

Optionally, ribs 228a,b and ribs 328a,b,c may extend toward the edges of adhesive substrate 218. Optionally there may be unbacked areas 335a,b,c,d of the adhesive substrate, for example on the edges (for example unbacked area 335c,d) and/or between ribs 228a,b and ribs 328a,b and ribs (for example, unbacked areas 335a,b). In some embodiments, an unbacked area (for example areas 335a,b) may be located between the skin of a user and the adjacent surface of the infuser and/or beyond an edge 325 of the infuser (for example areas 335c,d).

In the exemplary embodiment of FIG. 3, adhesive substrate 218 is optionally configured to avoid unintentional adhesion of substrate 218 to the infuser. For example, edges of unbacked areas of substrate 218 are optionally located away from the surface of the infuser. For example, the edges of the unbacked areas 335c,d extend beyond edge 325 of the infuser surface.

Figure 4A:
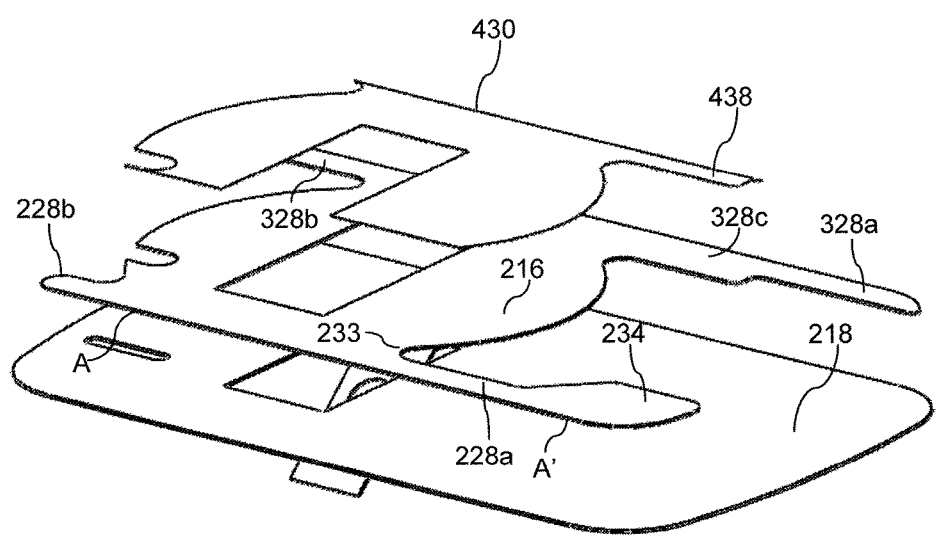
FIG. 4A is a exploded view of an exemplary embodiment of an adhesive system.

FIG. 4A is an exploded view of adhesive substrate 218, stiffener 216, and an infuser/adhesive interface 430 (where adhesive substrate 218 and/or stiffener 216 are attached to the adjacent surface of the infuser). In some embodiments, interface 430 may be entirely or mainly around the needle insertion point and/or the proximity sensor. Optionally, an extension 438 of the interface 430 may attach a portion of rib 328c to the adjacent surface. Attaching a portion of ribs 328c to the adjacent surface may for example increase the rigidity of the adhesion of injection location 226 to the user. Optionally, all or some of ribs 228a,b, and/or 328a,b,c may be attached and/or unattached to the adjacent surface of the infuser. Leaving ribs 228a,b and/or 328a,b,c fully and/or partially unattached may allow adhesive substrate 218 to conform more to the skin of the user.

In some embodiments, interface 430 may not surround the proximity sensor and/or the needle insertion point (for example when the top of the proximity sensor reaches the edge 325 of the adjacent surface [as illustrated in FIG. 3] then interface 430 may have an empty space above the proximity sensor as illustrated in FIG. 4A). In some embodiments, the stiffener may be used to lend stability where the adhesive substrate is not attached to the adjacent surface of the infuser. For example, stiffener 216, fills in the empty space above the proximity sensor.

In some embodiments, part or the entire stiffener 216 may extend away from needle insertion point 226 and or proximity sensor 224. Optionally, part of the extension may be attached to the adjacent surface of the infuser, for example section of rib 328c is attached to the adjacent surface by an extension 438 of interface 430. Optionally, parts of stiffener 216 may be affixed to part of the adhesive substrate 218 but not attached to the adjacent surface of the infuser. Optionally, parts of stiffener 216 may intervene between substrate 218 and the adjacent surface of the infuser and/or may protrude out from edge 325 of the infuser.

In some embodiments, a portion of stiffener 216 may support substrate 218 adjacent to a peeling tab 242a. For example, rib 328b may supply an opposing force pulling adhesive 218 from tab 242b as cover 222b is peeled away substrate 218. In some embodiments, cover 222a,b and/or tabs 242a,b may be configured to avoid liner tear. For example, the shape may encourage pulling along a rolling line. For example a tab may be located at a sharp and/or rounded corner of the cover.

Figure 4B:
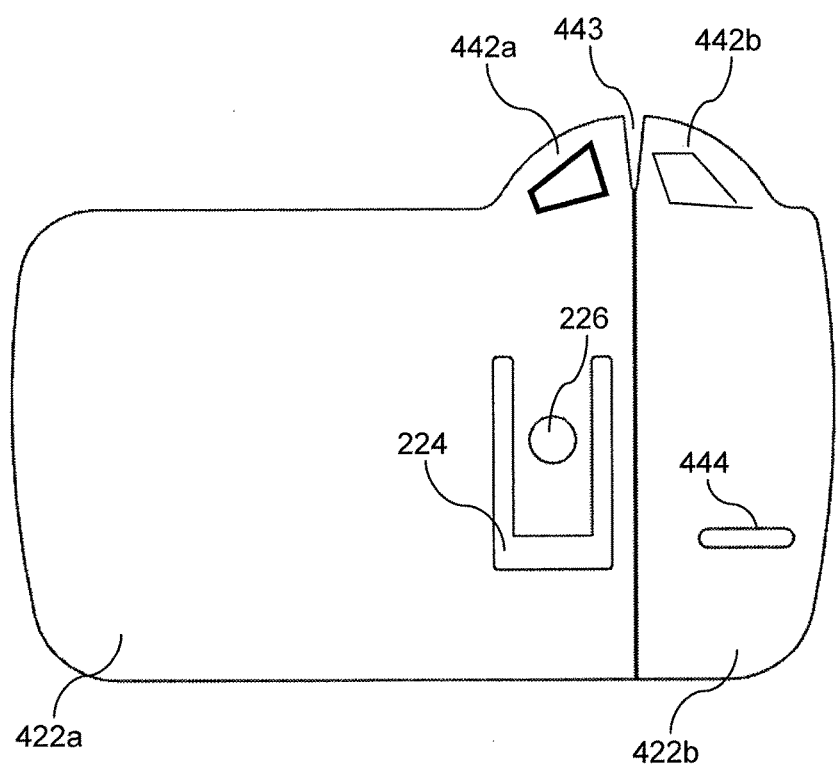
FIG. 4B is a projection view of an exemplary embodiment of an adhesive cover.
Figure 5A:
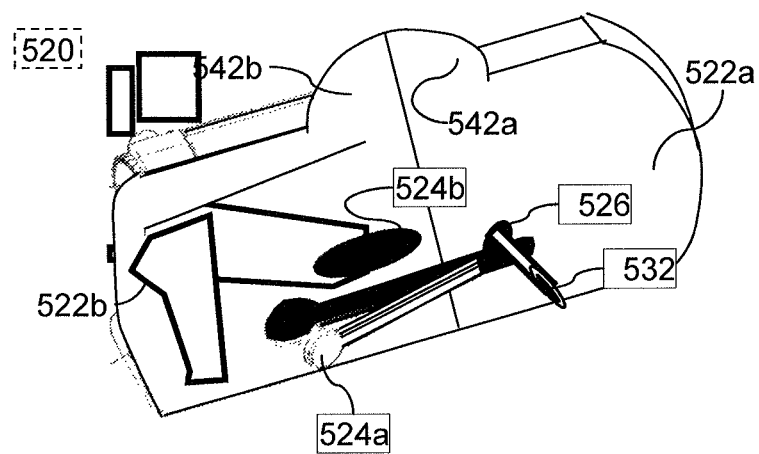
FIG. 5A is a perspective view of an exemplary embodiment of an adhesive cover on an infuser having an attaching interface surrounding a needle insertion point.

FIG. 4B illustrates an exemplary embodiment of a two part adhesive cover 422a,b that may be used, for example with exemplary infuser embodiment 220. Removal tabs 442a,b are located near a battery insulator slit 444. For example, when a user grasps removal tab 442b and pulls up, he may get good leverage to pull out a battery insulator strip attached to cover 422b and passing through slit 444. A triangle shaped notch 443 between tabs 442a,b indicates to a user that separate tabs 442a,b remove respective parts of adhesive cover 442a,b Exemplary Interface Surrounding Proximity Sensors and/or Needle Insertion Point FIG. 5A is a perspective view of an alternative exemplary embodiment 520 of an infuser. In embodiment a mechanical skin proximity sensor 524a and an optical skin proximity sensor 524b are located at a distance from an edge of the adjacent surface configured for connection to the skin of a user. Optionally, in embodiment 520, the needle insertion point and/or the sensor location are entirely surrounded by the interface attaching the adhesive matrix to the infuser.

Figure 5B:
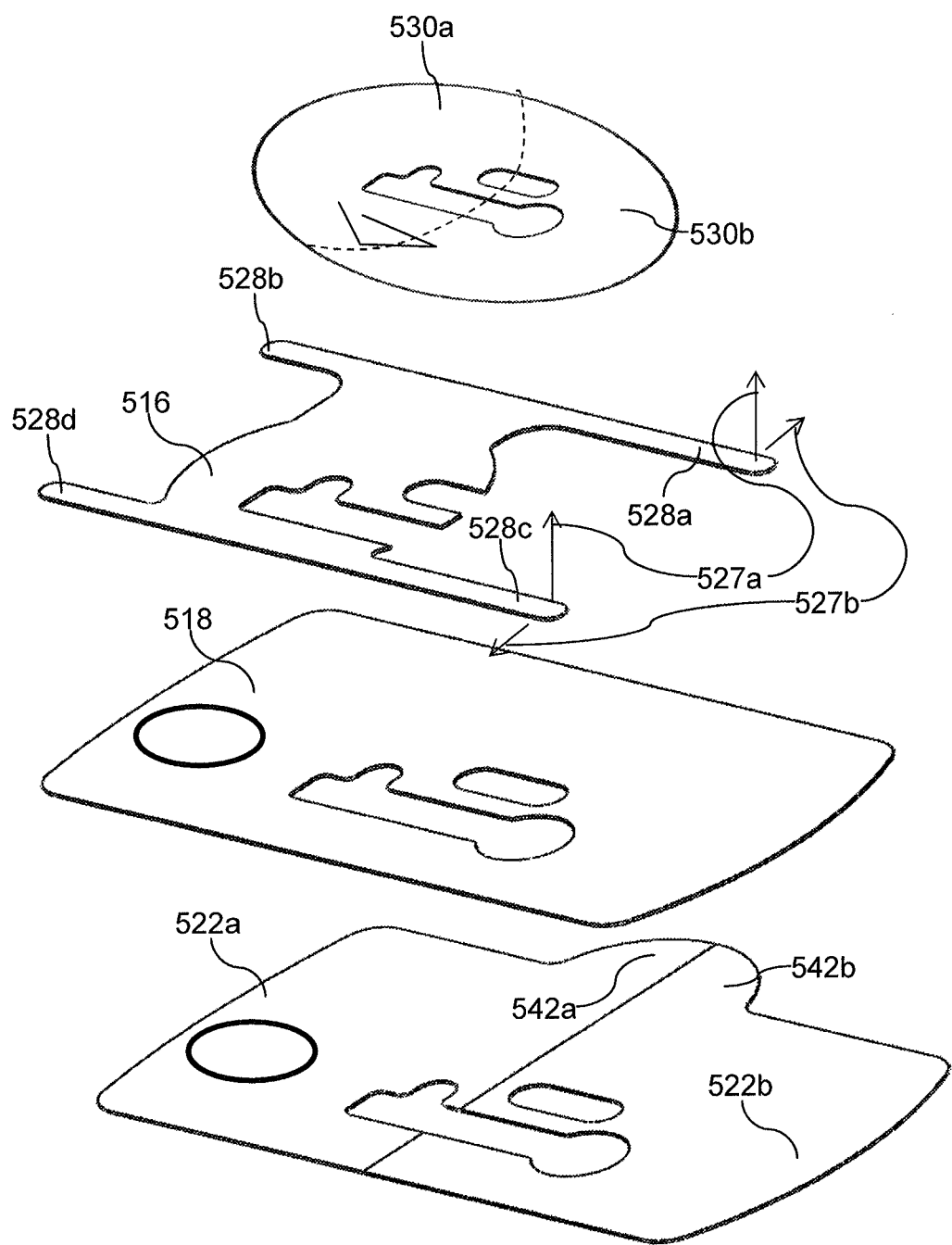
FIG. 5B is a exploded view of an exemplary embodiment of an adhesive system for an infuser having an attaching interface surrounding a needle insertion point.

FIG. 5B is an exploded view of four layers of an adhesive structure that may be used for example with embodiment 520. In some embodiments, an interface 530a,b may surround skin proximity sensors 524a,b and/or needle insertion point 526. In some embodiments part of an interface 530a may attach a stiffener 516 to an adjacent surface of an infuser and an adhesive substrate 518 to stiffener 516. Alternatively or additionally, part of the interface 530b may attach the adhesive substrate 518 directly to the adjacent surface of the infuser. In some areas, alternatively or additionally, there may be a padding layer between the adhesive substrate and the adjacent surface of the infuser.

In some embodiments stiffener 516 may be biased. For example ribs 528a,c may be biased upward 527a away from the user's skin. Alternatively or additionally, 528a,c may be biased outward 527b, extending substrate 518 and/or holding it taut. Optionally, when the infuser is held above the skin of the user, ribs 528a,c may hold the skirt of substrate 518 upwards away from the skin attaching surface, preventing it from folding downward.

In some embodiments ribs 528a,b,c,d may extend from an attached area 530a,b toward the periphery of adhesive substrate 518.

FIG. 5A shows a hypodermic needle 532 extending out of a needle insertion hole 526. A two part adhesive cover 522a,b includes respective peeling tabs 542a,b.

Options, Alternatives and Additional Aspects

Figure 6A:
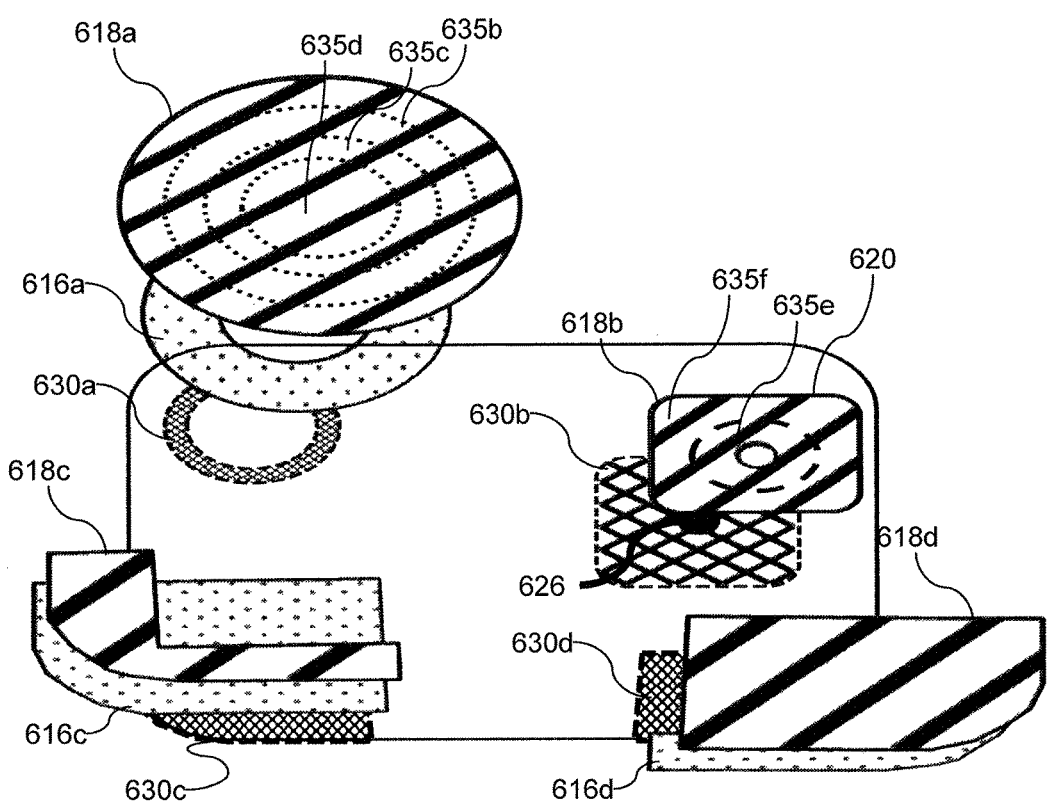
FIG. 6A is a exploded view of an exemplary embodiment of an adhesive system having discrete sections.
Figure 6B:
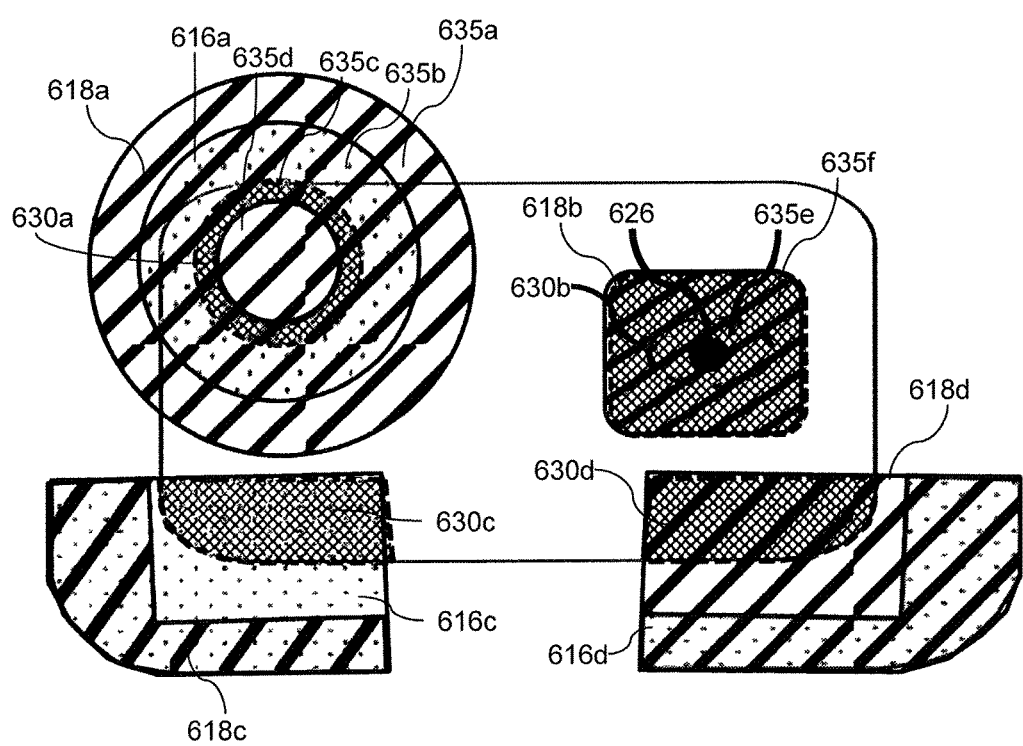
FIG. 6B is a schematic view through layers of an exemplary embodiment of an adhesive system having discrete sections.

FIGS. 6A and 6B show a few alternative configurations for an adhesive system. For example, single device may have a few discrete adhesive systems connected to different points on one or more surfaces adjacent to a user. Tabs for activating the various discrete adhesive systems may also be discrete and/or they may be integrated for intuitive synchronized activation. Alternatively or additionally, a stiffener may be attached to a surface of the device and the adhesive affixed to the stiffener. Alternatively or additionally, the adhesive substrate may be attached directly to a surface of the device and the stiffener affixed to part of the adhesive substrate. Alternatively or additionally, all or part of the adhesive substrate and/or the stiffener may intervene between the skin of the user and the adjacent surface of the infuser. Alternatively or additionally, all or part of the stiffener and/or the adhesive substrate may project over the edge of the surface of the infuser.

In the exemplary embodiment of FIGS. 6A and 6B, four discrete adhesive systems are illustrated attached to a single surface of a device. For example, an interface 630a may attach a portion of a stiffener 616a to a part of the adjacent surface of the infuser. Optionally, a portion of an adhesive substrate 618a may be affixed to stiffener 616a and/or attached to the interface 630a. For example adhesive substrate 618a may be have areas of different levels of attachment: an outer unbacked skirt area 635a which extends outward beyond the boundaries of both stiffener 616a and interface 630a; a stiffened flexible skirt area 635b affixed to the stiffener at a location beyond the boundaries of the interface 630a inward and/or outward; a fully attached area 635c which is a affixed to stiffener 616a at a location where stiffener 616a is attached to surface 620 via interface 630a, and an inner unbacked area 635*d* completely and/or partially surround by interface 630*a*. All or part of areas 635*a,b,d* may optionally be located between surface 620 and the skin of a user and/or may extend beyond the edges of adjacent surface 620 of the infuser.

In some embodiments, an adhesive substrate may be attached in all or in part directly to an adjacent surface of an infuser. For example, substrate 618*b* is attached directly to the surface of the infuser in interface 630*b* in the vicinity of needle insertion point 626. Optionally an area 635*e* of interface 630*b* near insertion point 626 may be stiff. Optionally an area 635*f* of interface 630*b* further from insertion point 626 may be relatively flexible. For example in area 635*f* flexible padding may intervene between the surface of the infuser and substrate 618*b* (in the exemplary embodiment of FIGS. 6A, B the boundary between areas 635*e* and 635*f* is marked by a dashed line). Optionally, there may be a rib of stiff interface to a peeling location on the edge of the interface. The peeling location may be for peeling the adhesive from the skin of the user and/or for peeling an adhesive cover from the adhesive.

In some embodiments, an adhesive substrate may be affixed to a flexible stiffener extending away from an interface. For example an adhesive substrate 618*c* is shown affixed to a portion of flexible stiffener 616*c* extending away from an interface 630*c*. In the example of FIGS. 6A, B substrate 618*c* is show extending beyond surface 620 of the infuser. Alternatively or additionally, a portion of an adhesive substrate may be affixed to a stiffener layer away from an attachments interface but located between the user's scan and adjacent surface of the infuser. For example, intervention of the stiffener between the matrix and the user may help prevent unintended adhesion of the substrate to the infuser.

In some embodiments, a stiffener layer may not be directly attached to the infuser. For example, stiffener 616*d* is not directly attached to the infuser. Stiffener 616*d* is affixed to adhesive substrate 618*d* which is attached to the infuser at interface 630*d*.

In some embodiments, the adhesive substrate may have a skirt partially surrounded the interface joining the adhesive to the device. For example, adhesive substrates 618*c* and 618*d* have skirts surrounding the respective interfaces 630*c* and 630*d* on only two sides. Alternatively or additionally, the skirt may surround the interface on all sides. For example, areas 335*a,b,c,d* surround interface 430 on all sides.

Optionally, the surface of the infuser that is adjacent to the user's skin may be shaped to facilitate placing flat against the skin. A stiffener may also optionally be designed for conforming to the skin surface during placement. Optionally, the infuser may be shaped to encourage proper placement of the device. Optionally the infuser may be designed to avoid placement of the needle insertion point and/or the skin proximity sensor near a fold in the skin of the user.

Exemplary Method of Mounting an Adhesive on an Infuser

Figure 7:
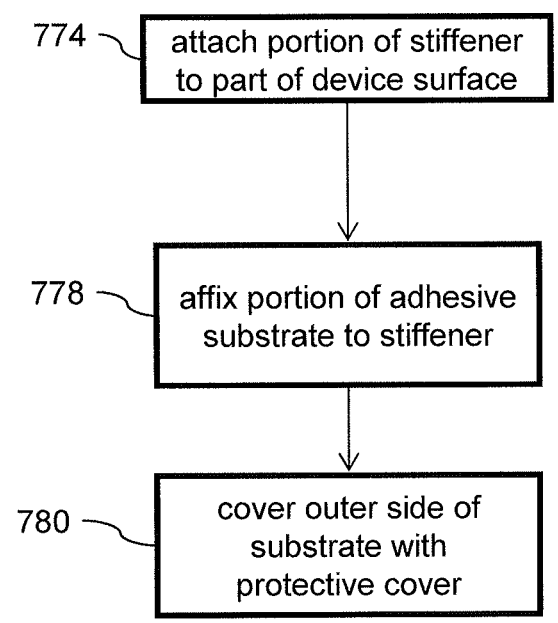
FIG. 7 is a flow chart illustration of an exemplary embodiment of a method for attaching an adhesive system to an infuser.

FIG. 7 is a flow chart illustrating an exemplary method of attaching an adhesive system to an infuser. The method includes bonding various layers of the adhesive system to one another and/or to the infuser.

The method may start, for example, by attaching 774 a portion of the stiffener to a surface of the infuser. Alternatively or additionally, the stiffener may be attached to a coupling that can be removably attached to the infuser.

In some embodiments, an adhesive substrate may be affixed 778 to the stiffener. Alternatively or additionally, the adhesive substrate may be affixed directly to the infuser.

In some embodiments an adhesive surface may be covered 780 with a protective cover.

General

In some embodiments, some layers may be supplied in a prebonded state. For example, the adhesive substrate may be supplied with the adhesive cover already in place. Optionally the adhesive substrate and/or the stiffener layer may also be supplied in a precut form.

It is expected that during the life of a patent maturing from this application many relevant adhesives, substrates and stiffener materials will be developed and the scope of the terms are intended to include all such new technologies a priori. As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for anchoring a location on a surface of a medical infusion device to a skin of a user, the system comprising:
   an adhesive substrate for adhering to the skin of the user;
   a stiffener directly covering a portion of the adhesive substrate; and
   an interface directly covering a portion of the stiffener, such that the stiffener is interposed between the interface and the adhesive substrate and is arranged below a horizontal plane of the interface and above a horizontal plane of the adhesive substrate, the interface attaching a portion of said adhesive substrate to the surface of the device,
      wherein said adhesive substrate is a separate and distinct layer from said stiffener and said interface;
      wherein said adhesive substrate includes a skirt extending beyond said interface, said skirt being flexibly attached to said interface; and
      wherein the stiffener directly covers and stiffens a portion of said skirt, said stiffener being less flexible than said substrate.

2. The system of claim 1, wherein said stiffener inhibits folding of said skirt under an out of plane bending force.

3. The system of claim 2, wherein said stiffener inhibits folding of said skirt due to gravity.

4. The system of claim 3, wherein said stiffener suspends said skirt against a gravity force.

5. The system of claim 3, wherein said stiffener is biased away from a skin attaching surface of said substrate.

6. The system of claim 1, further including:
   an adhesive cover, and
   a tab for peeling said adhesive cover from said substrate and
wherein said stiffener supports said substrate adjacent to said tab, supplying an opposing force when peeling said cover away from said substrate.

7. The system of claim 6, wherein said tab is located on said skirt.

8. The system of claim 6, wherein said stiffener is stiff enough to resist a force on said substrate caused by peeling of said cover.

9. The system of claim 1, further including:
   a start location for removal of the system from the user and wherein said stiffener extends along a peeling line to said start location, facilitating removing of said adhesive substrate from the user's skin.

10. The system of claim 9, wherein said start location is on said skirt.

11. The system of claim 9, wherein said stiffener includes a sharp turn between said peeling line and said interface.

12. The system of claim 1, wherein said stiffener interposes between at least a part of the surface and a remaining portion of said substrate.

13. The system of claim 1, wherein said stiffener extends beyond a boundary of said surface.

14. The system of claim 1, wherein said substrate extends beyond a boundary of said stiffener.

15. The system of claim 1, wherein said substrate, is divided into a plurality of discrete portions and wherein each of said portions is joined to a separate respective subsurface of said surface.

16. The system of claim 1, wherein said interface surrounds the location on at least two sides.

17. The system of claim 1, wherein said stiffener includes one or more ribs extending from said interface toward an edge of said substrate.

18. The system of claim 1, wherein an unbacked section of said substrate is surrounded on at least two sides by said stiffener.

19. The system of claim 1, where said stiffener is attached to the surface of the device and said substrate is affixed to said stiffener.

20. The system of claim 1, wherein an unbacked skirt of said substrate surrounds the surface on at least two sides.

21. The system of claim 1, wherein said substrate is not directly attached to said surface.

22. A system for anchoring a location on a surface of a medical infusion device to a skin of a user the system comprising:
   a flexible adhesive substrate for adhering to the skin of the user;
   an interface attaching said adhesive substrate to the surface of the device and wherein said interface includes at least one relatively flexible region and at least one less flexible region;
   a stiffener directly covering a portion of the adhesive substrate, wherein the interface covers a portion of the stiffener, such that a portion of the stiffener is interposed between the interface and the adhesive substrate and is arranged below a horizontal plane of the interface and above a horizontal plane of the adhesive substrate;
   an adhesive cover; and
   a tab for peeling said adhesive cover from said adhesive substrate,
      wherein said adhesive substrate is a separate and distinct layer from said stiffener and said interface,
      wherein the stiffener is affixed to an unattached portion of said adhesive substrate, and
      wherein said stiffener supports said adhesive substrate adjacent to said tab, supplying an opposing force when peeling said adhesive cover away from said adhesive substrate.

23. The system of claim 22, wherein said interface is attached to a portion of said adhesive substrate.

24. The system of claim 22, further including:
   a start location for removal of the system from the user and
wherein said stiffener extends along a peeling line to said start location, facilitating removing of said adhesive from the user's skin.

* * * * *